(12) United States Patent
Harnack et al.

(10) Patent No.: US 7,785,901 B2
(45) Date of Patent: Aug. 31, 2010

(54) METHOD OF ATTACHING HYDROPHILIC SPECIES TO HYDROPHILIC MACROMOLECULES AND IMMOBILIZING THE HYDROPHILIC MACROMOLECULES ON A HYDROPHOBIC SURFACE

(75) Inventors: Oliver Harnack, Stuttgart (DE);
William E. Ford, Stuttgart (DE); Jurina Wessels, Stuttgart (DE); Akio Yasuda, Stuttgart (DE)

(73) Assignee: Sony Deutschland GmbH, Cologne (DE)

( * ) Notice: Subject to any disclaimer, the term of this patent is extended or adjusted under 35 U.S.C. 154(b) by 987 days.

(21) Appl. No.: 10/631,351

(22) Filed: Jul. 31, 2003

(65) Prior Publication Data

US 2004/0023287 A1 Feb. 5, 2004

(30) Foreign Application Priority Data

Aug. 2, 2002 (EP) .................................. 02017380

(51) Int. Cl.
*G01N 33/553* (2006.01)
(52) U.S. Cl. .................... 436/525; 436/518; 436/524; 427/457
(58) Field of Classification Search ............... 436/518, 436/519, 524, 525, 73, 84; 422/50, 61; 435/174, 435/283.1, 287.8, 287.2; 427/457, 498, 501, 427/584
See application file for complete search history.

(56) References Cited

U.S. PATENT DOCUMENTS

| | | | | |
|---|---|---|---|---|
| 5,516,703 | A * | 5/1996 | Caldwell et al. | 436/532 |
| 5,610,287 | A * | 3/1997 | Nikiforov et al. | 536/24.3 |
| 5,688,642 | A * | 11/1997 | Chrisey et al. | 435/6 |
| 5,747,244 | A * | 5/1998 | Sheridan et al. | 435/6 |
| 6,030,782 | A * | 2/2000 | Anderson et al. | 435/6 |
| 6,087,452 | A | 7/2000 | Stewart et al. | |
| 6,361,944 | B1 | 3/2002 | Mirkin et al. | |
| 6,579,721 | B1 * | 6/2003 | Natan et al. | 436/164 |
| 2002/0034756 | A1 | 3/2002 | Letsinger et al. | |
| 2002/0050220 | A1 * | 5/2002 | Schueller et al. | 101/486 |
| 2002/0065242 | A1 * | 5/2002 | Ford et al. | 514/44 |
| 2002/0117659 | A1 * | 8/2002 | Lieber et al. | 257/14 |
| 2003/0187237 | A1 * | 10/2003 | Chan et al. | 536/22.1 |
| 2003/0211488 | A1 * | 11/2003 | Mirkin et al. | 435/6 |
| 2003/0215865 | A1 * | 11/2003 | Mayer et al. | 435/6 |

FOREIGN PATENT DOCUMENTS

WO   WO 02 46760   6/2002

OTHER PUBLICATIONS

Berning et al. 198Au-Labeled Hydroxymethyl Phosphines as Models for Potential Therapeutic Pharmaceuticals, 1998, Nuclear Medicine and Biology, vol. 25, pp. 577-583.*

(Continued)

*Primary Examiner*—Melanie J Yu
(74) *Attorney, Agent, or Firm*—Oblon, Spivak, McClelland, Maier & Neustadt, L.L.P.

(57) ABSTRACT

The present invention is related to a method of attaching hydrophilic species to hydrophilic macromolecules and immobilizing the hydrophilic macromolecules on a hydrophobic surface, to a nano-assembly and to uses of the nano-assembly.

19 Claims, 10 Drawing Sheets

Height scale: 40 nm

OTHER PUBLICATIONS

Brown et al. Seeding of Colloidal Au Nanoparticle Solutions 2. Improved Control of Particle Size and Shape, 2000, Chem. Mater., vol. 12, pp. 306-313.*

Klein et al., Ordered Stretching of single molecules of deoxyribose nucleic acid between microfabricated polystyrene lines, 2001, Applied Physics Letters, vol. 78, No. 16, pp. 2396-2398.*

Braun et al: "DNA-templated assembly and electrode attachment of a conducting silver wire" Nature MacMillan Magazines, US, vol. 6669, No. 391, pp. 775-778, XP002079216 Feb. 1998 ISSN: 0028-0836.

* cited by examiner

METHOD OF ATTACHING HYDROPHILIC SPECIES TO HYDROPHILIC MACROMOLECULES AND IMMOBILIZING THE HYDROPHILIC MACROMOLECULES ON A HYDROPHOBIC SURFACE

With the advent of nanotechnology the attachment and assembly of molecules/macromolecules in a predefined pattern has become the focus and subject of intense research. In this respect, macromolecules, like nucleic acids and proteins, have been studied in terms of their behavior in solution and when attached to surfaces (Y. Xia et al., Chemical Reviews 99 (1999) 1823-1848). With a continuing strive for miniaturization there is a growing need for the development of techniques that allow the assembly of devices based upon single molecules. To this end nucleic acids have been immobilized on both hydrophilic and hydrophobic substrate materials. The immobilization of DNA on hydrophilic surfaces was reported on plasma treated silicon oxide (O. Harnack, W. E. Ford, J. M. Wessels, European Patent Publication No. EP 1. 207 207 A1), amino-silane treated surfaces (J.-F. Allemand et al., Biophysical Journal 73 (1997) 2064-2070), mica surfaces and others. WO 95/15970 describes a method for the immobilization of nucleic acid molecules on polystyrene surfaces that had been made hydrophilic by the addition of appropriate chemical functionalities.

The immobilization of nucleic acids on hydrophobic surfaces has been reported for various polymer surfaces like polymethylmetacrylate (PMMA), polystyrene and others (J.-F. Allemand et al., Biophysical Journal 73 (1997) 2064-2070). Klein et al., reported on the attachment of DNA to lithographically patterned, hydrophobic polystyrene lines (D. C. G. Klein et al., Appl. Phys. Lett., 78, 16 (2001) 2396-2398). Recently, Nakao et al. reported on the succesful DNA immobilization on polyvinylbutyral, poly(vinylcarbazole) and polyphenazasiline coated surfaces (H. Nakao et al., NanoLetters 2 (2002) 475-479). U.S. Pat. No. 5,747,244 describes the immobilization of nucleic acid probes on polystyrene surfaces that have been pretreated with a polypeptide that has a multiplicity of reactive primary amino groups and/or sulfhydryl or carboxylate groups that allow for a covalent bonding of the nucleic acid to the polypeptide adsorbed to the surface.

The fabrication of nano-devices not only requires the specific assembly of molecules/macromolecules but, possibly, also the decoration of the assembled molecules/macromolecules by appropriate species, such as metal nanoparticles, that confer specific qualities onto the molecular assemblies. By metallization, e.g., of linear molecular assemblies, conducting nanowires may be fabricated. So far a metallization of nucleic acids has only been reported for DNA on hydrophilic surfaces (plasma treated $SiO_2$ surfaces, silanised surfaces). For example Braun et al. report on the Ag-metallization of DNA on $SiO_2$ (E. Braun et al., Nature 1998, 391, 775). Furthermore DNA has been metallized with Pt, being immobilized on $SiO_2$ (J. Richter et al., Appl. Phys. Lett. 2001, 78, 536), and Ford et al. (Adv. Mater. 2001, 13, 1793) report on the Pt-metallization of DNA immobilized on oxygen plasma treated $SiO_2$. In many applications, however, it is desirable to have a hydrophobic surface as the substrate on which all further reactions are performed. None of the above cited pieces of prior art, however, provide a teaching as to how to perform the above reactions, like immobilization and decoration with species, on hydrophobic surfaces. Furthermore the methods described in the prior art in relation to hydrophilic surfaces, require long reaction and processing times. Additionally the nano-devices produced so far according to the prior art have not yielded satisfactory results, in terms of the dimensions of the devices thus fabricated (elongation of nanowires etc.) and the presence or rather absence of defects.

Accordingly it has been an object of the present invention to provide for a method for producing nano-devices, which method is less time consuming and achieves more perfect nano-devices. Furthermore it is an object of the present invention to provide for a method whereby the attachment process of the species to the macromolecules does not disturb the immobilization of the macromolecules on the surface. Furthermore it has been an object of the present invention to provide a method that allows a specific decoration of the macromolecules with species and avoids the non-selective binding of the species to the surface.

All these objects are solved by a method of attaching hydrophilic species to hydrophilic macromolecules and immobilizing the hydrophilic macromolecules on a hydrophobic surface, said method comprising the steps:
  exposing hydrophilic macromolecules to hydrophilic species whereby the hydrophilic species are attached to the hydrophilic macromolecules,
  providing a hydrophobic surface,
  immobilizing the hydrophilic macromolecules on the hydrophobic surface.

The objects of the present invention are also solved by a method of attaching hydrophilic species to hydrophilic macromolecules immobilized on a hydrophobic surface, said method comprising the steps:
  providing a hydrophobic surface,
  immobilizing hydrophilic macromolecules on the hydrophobic surface,
  exposing the hydrophilic macromolecules immobilized on the hydrophobic surface to hydrophilic species, whereby the hydrophilic species are attached to the hydrophilic macromolecules.

In one embodiment, the hydrophilic species comprise nanoparticles.

In one embodiment, the hydrophilic species are in solution.

Preferably, the method according to the present invention comprises the additional step:
  growing the attached hydrophilic species to a larger size, wherein, more preferably, growing the attached hydrophilic species to a larger size is achieved by exposing the attached hydrophilic species to an electroless plating solution.

In one embodiment, immobilizing the hydrophilic macromolecules on the hydrophobic surface occurs by applying the hydrophilic macromolecules to the hydrophobic surface.

In one embodiment, applying the hydrophilic macromolecules to the hydrophobic surface occurs by a process selected from spin-coating, dip-coating, drop-casting, stamping, molecular combing, spraying-techniques, inkjet-printing and doctor-blading.

In one embodiment, exposing the hydrophilic macromolecules to hydrophilic species, whereby the hydrophilic species are attached to the hydrophilic macromolecules, occurs over a period of time between 1 second and 120 minutes, wherein, preferably exposing the hydrophilic macromolecules to hydrophilic species occurs over a period of time between 10 seconds and 10 minutes.

In one embodiment of the invention, the solution is a solution of the hydrophilic species in water or of the hydrophilic species in a water-miscible organic solvent/water mixture, wherein preferably the water-miscible organic solvent is an alcohol, more preferably methanol or ethanol or a combination of both.

Preferably, water has a contact angle on the hydrophobic surface in the range of from 30° to 110°.

More preferably, water has a contact angle on the hydrophobic surface in the range of from 60° to 110°.

Contact angles can be measured by any state-of-the-art contact angle goniometer. In a prefered embodiment they are measured by a goniometer of Ramé-Hart, Inc., US, more preferably model 100-00-(115/220)-S.

In one embodiment, the hydrophilic species is selected from the group comprising water soluble metal nanoparticles, semiconductor nanoparticles and dielectric (insulator) nanoparticles, hydrophilic clusters and metallic complexes.

In one embodiment of the method according to the present invention, the nanoparticle has a core and comprises a metal or metal oxide in the core, where the metal is selected from the group comprising Fe, Co, Ni, Cu, Ru, Rh, Pd, Os, Ir, Ag, Pt, Au or combinations, especially alloys of these metals.

In one embodiment, the hydrophilic macromolecules are selected from the group comprising nucleic acids, proteins, dendrimers, latex spheres, polyelectrolytes, and water-soluble polymers.

Preferably, the nucleic acid is selected from the group comprising DNA, RNA, PNA, CNA, oligonuclotides, oligonucleotides of RNA, A-DNA, B-DNA, Z-DNA, polynucleotides of DNA, polynucleotides of RNA, T-junctions of nucleic acids, triplexes of nucleic acid, quadruplexes, of nucleic acids, domains of non-nucleic acid polymer-nucleic acid block-copolymers and combinations thereof.

More preferably, the nucleic acid is double-stranded or single-stranded.

In a preferred embodiment, the hydrophilic species is selected from the group comprising tris(hydroxymethyl) phosphine-gold nanoparticles (THPAuNPs).

Preferably, the electroless plating solution comprises a gold salt and a reducing agent.

The objects of the present invention are also solved by a nano-assembly, comprising
a hydrophobic surface
hydrophilic macromolecules immobilized on the hydrophobic surface
a hydrophilic species attached to the hydrophilic macromolecules.

The objects of the present invention are furthermore solved by a nano-assembly produced by the method according to the present invention.

The objects of the present invention are furthermore solved by a nucleic acid and/or protein wire produced according to the method of the present invention, having a mean diameter of from between 2 nm-500 nm, and being completely decorated by hydrophilic species. Preferably the mean diameter is in the range of from 5 nm-200 nm.

The objects of the present invention are furthermore solved by the use of a nano-assembly according to the present invention as a nanoscale element in a device, wherein preferably, the function of the nanoscale element is selected from the group comprising interconnect, sensor, optical absorber, actuator, transducer, and memory.

As used herein the term "decoration of macromolecules by or with appropriate species" is to be understood as interchangeable in its meaning with "attaching appropriate species to macromolecules". It is furthermore to be understood that, although the method according to the present invention is recited comprising the aforementioned three steps, no specific sequence is envisaged, i.e. the three steps can be performed in any order, with the restriction that the step of providing a hydrophobic surface always precedes the step of immobilizing the hydrophilic macromolecules on the hydrophobic surface.

Using the method according to the present invention the immobilized macromolecules surprisingly withstand the attachment step of the hydrophilic species, and the density of non-selectively bound hydrophilic species to the hydrophobic surface can be reduced without reducing the degree of decoration of immobilized macromolecules with hydrophilic species (i.e. the attachment step is highly specific). Furthermore the duration of the attachment step can be reduced to only a few minutes, which is a significant advantage over the state of the art attachment approaches on hydrophilic surfaces. For example a complete metallization of DNA molecules, using the inventive method, is achievable using a short attachment step of less than five minutes, plus the time for an electroless plating step. Another advantage of the method according to the present invention is for example a higher amount of elongated wires with fewer defects when compared to the state of the art assemblies.

Statistically, using the method according to the present invention allows fabrication of significantly longer wires whose mean diameter can be varied over a wider range and having fewer defects when compared to the state of the art methods. Furthermore the use of a hydrophobic substrate according to the present invention allows DNA metallization to be achieved using aqueous THPAuNP stock solutions, whereas poor results are obtained when hydrophilic substrates are used. This includes a higher degree of reproducibility.

Reference is now made to the figures wherein

FIG. 8b: SEM picture of THPAuNPs on electron-beam irradiated areas at higher magnification than for FIG. 8a.

Without wanting to be bound by any theory it is suggested that the mechanism behind the enhanced "binding" of water-soluble NPs to DNA on hydrophobic polymer surfaces might be driven by the tendency of the particles to join hydrophilic areas on the hydrophobic substrate surface. The immobilized DNA molecules represent such hydrophilic areas. This results in a driving force which supports the self-organisation/self-assembly of the nanoparticles along the DNA molecule. We do not exclude the possibility of additional binding mechanisms, which at the end contribute to the attachment of NPs to the DNA.

It is furthermore suggested that the presence of a water-miscible organic solvent, in particular of an alcohol enhances the reproducibility and the yield of the metallization process. A reason could be that the lower dielectric constant of a water-miscible organic solvent/water mixture in comparison to pure water reduces the electrostatic repulsion of the negatively charged THPAuNPs (c.f., S. L. Westcott et al., Langmuir 1998, 14, 5396). Also, the tendency of the particles to dissolve into the hydration shell surrounding the DNA, could be enhanced by adding a non-polar solvent to the NP/water mixture.

Figure 7A:
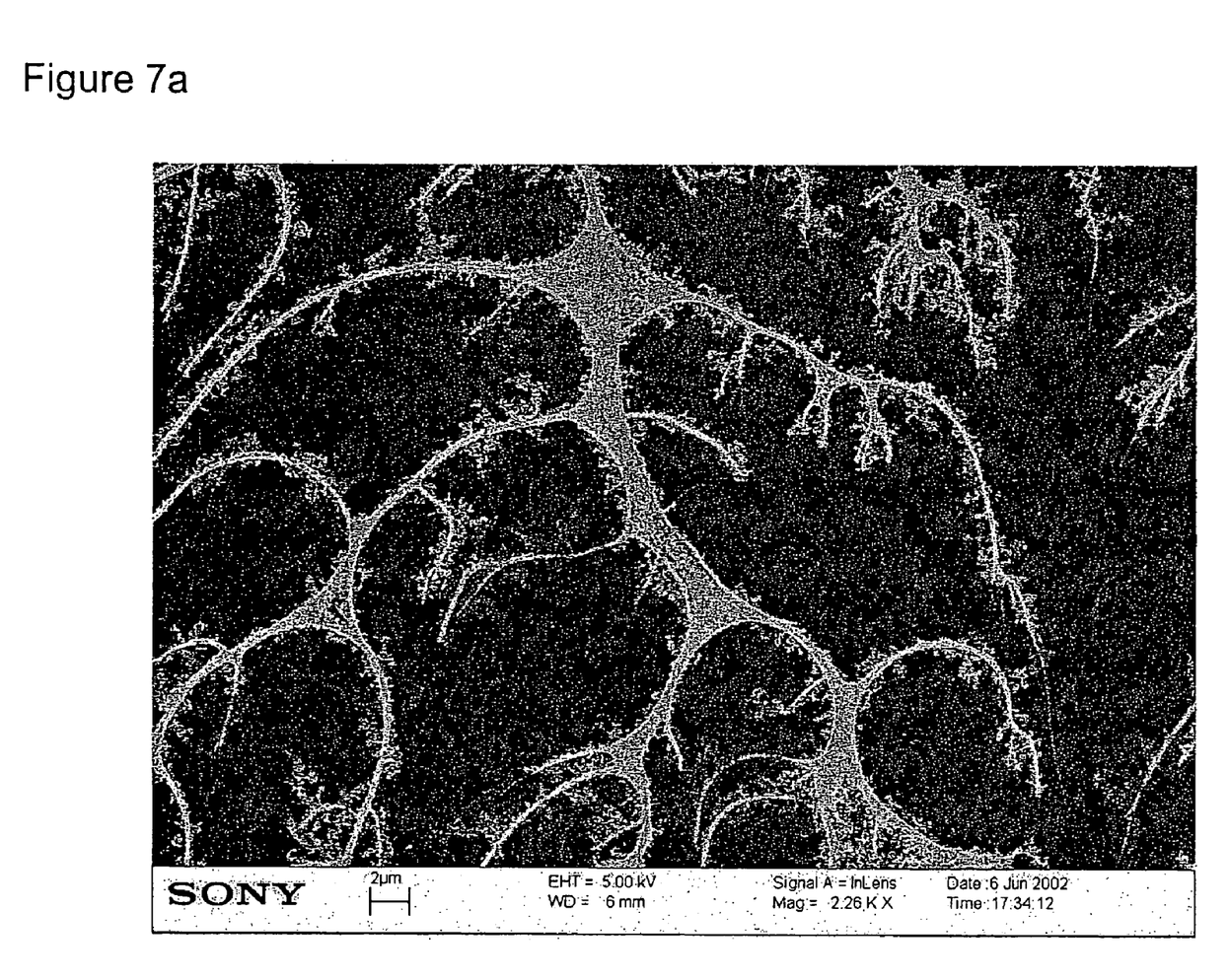
FIG. 7a shows an SEM picture of metallized DNA wires on polystyrene (treated according to one embodiment of the method according to the present invention). Metallic aggregations are embedded between DNA molecules
Figure 7B:
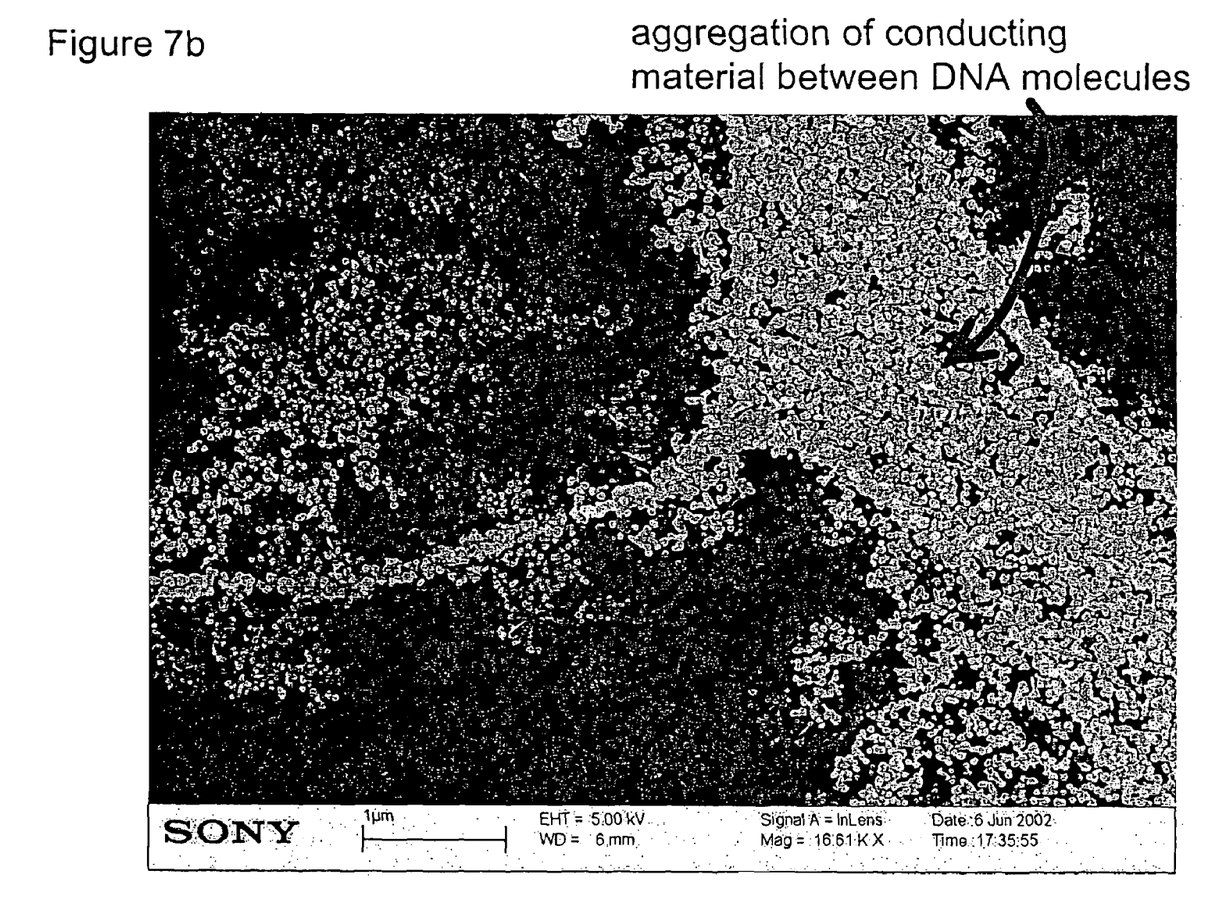
FIG. 7b shows an SEM picture of metallized DNA wires on polystyrene (treated according to one embodiment of the method according to the present invention) at higher magnification than for FIG. 7a. Metallic aggregations are embedded between DNA molecules.

A further observation in the SEM pictures may support the idea of driving forces, which are caused by hydrophilic-hydrophobic interactions. FIG. 7 shows a network of DNA molecules which were metallized by applying Step 1, 2, 3, 4b, and 5. The DNA molecules seem to span areas where NPs were collected in form of thin films. DNA molecules surround such areas and this leads to the conclusion that water could have been stabilized on such areas. This would lead to the observed aggregation of conducting material on the surface between DNA molecules.

Figure 8A:
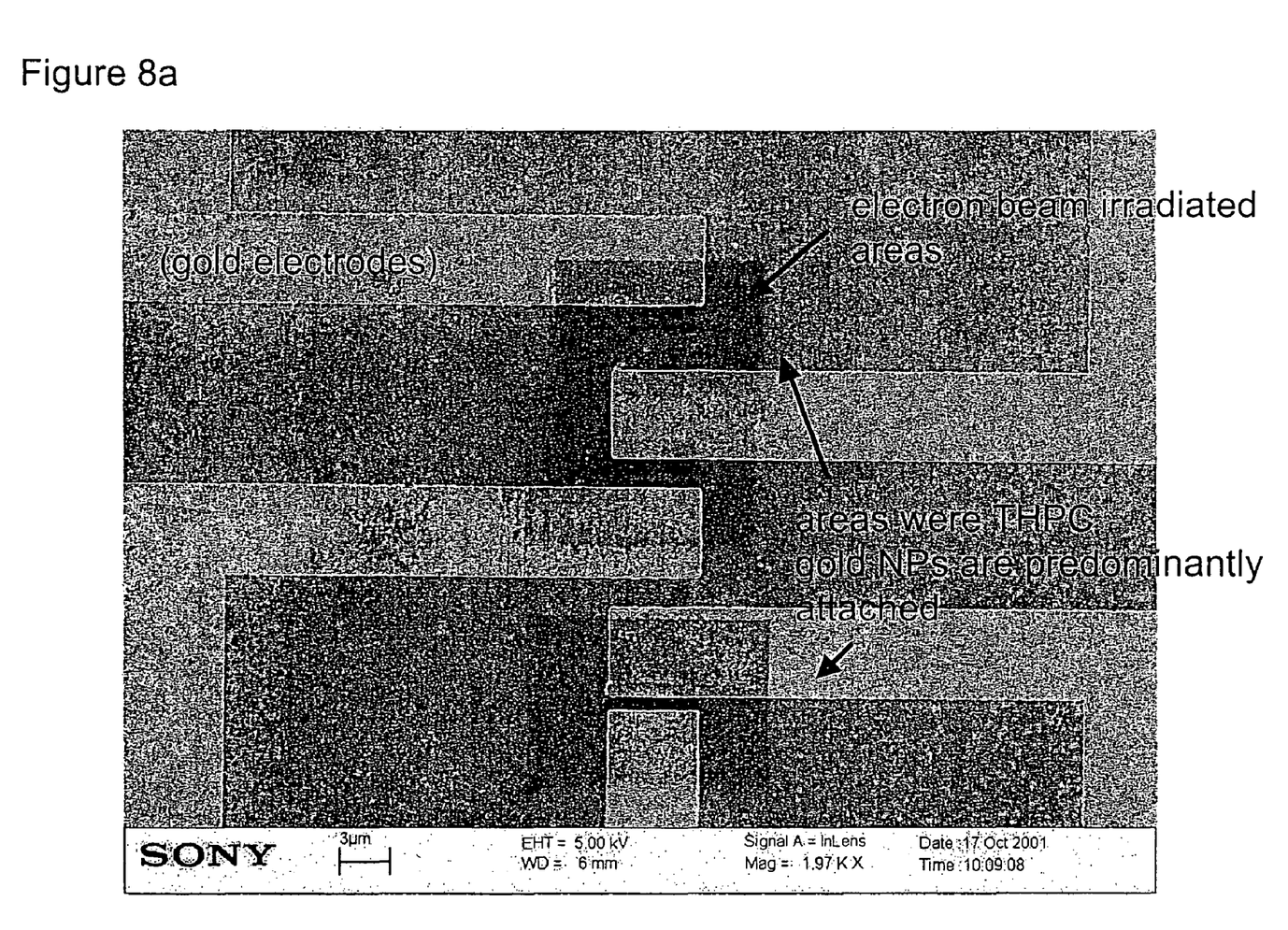
FIG. 8a shows an SEM picture of THPAuNPs on electron-beam irradiated areas.
Figure 8B:
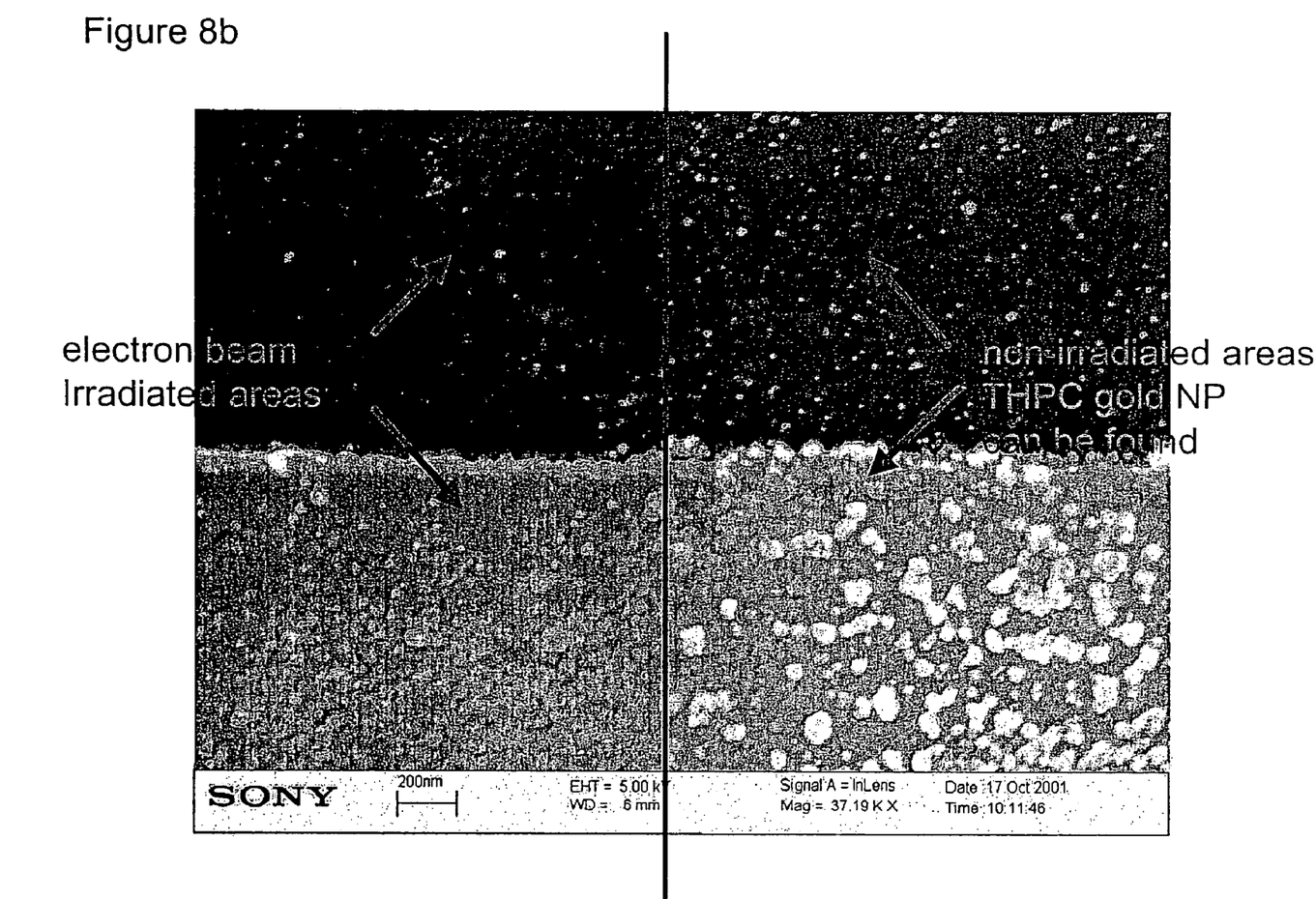

The THPAuNPs, which were used in an example procedure, showed reduced affinity to hydrophobic surfaces also in a different type of our experiment: $SiO_2$/Si surfaces were irradiated using the electron-beam of an SEM. It is known that a hydrophobic surface layer from amorphous carbon can be formed at high electron doses due to the decomposition hydrocarbon components from the vacuum background. In the experiments described below such electron-beam irradiated areas were treated with the water soluble gold NPs according to Step. 4a/b and 5 (for details see example 1) and fewer particles were found on the previously irradiated (now hydrophobic) areas (FIG. 8), which underlines the enhanced specificity of attachment of the hydrophilic species to the hydrophilic macromolecules, achieved by the present invention.

Although the following examples describe a scenario wherein hydrophilic species are attached to hydrophilic macromolecules immobilised on a hydrophobic surface, in principle, also the opposite case of attachment of hydrophobic species to hydrophobic macromolecules immobilised on hydrophilic surfaces should also be effective. No specific example, however, can be given for this case at this point in time.

The invention is now further described by reference to the following examples which are intended to illustrate, not to limit the scope of the invention.

EXAMPLE 1

Sample Preparation

All experimental results provided in the following section were achieved by using calf thymus DNA (ctDNA) molecules provided by SIGMA[17] or DNA ladder (Roche Diagnostics DNA Molecular. Weight Marker XVI, Cat. No. 1855638). The ctDNA was dissolved in sodium phosphate buffer (10 mM) to obtain an optical density of 1.26 at 258 nm wavelength and at 1 cm path length. The DNA ladder consists of a mixture of 12 blunt-ended, double-stranded DNA fragments covering the size range of 250 to 3000 base pairs and is provided as a 250 µg/mL solution in 10 mM Tris-HCl, 1 mM EDTA, pH 8.0. This solution was diluted with water to a concentration of 0.5 µg/ml before use.

In all cases, the substrate material was $SiO_2$ on Si. On top of these substrates, the polymer film was usually applied by spin coating. In the following, one drop of solution is regarded to have a volume of about 25 µl.

One embodiment of the method according to the present invention is performed as follows:

Step 1

1.2 g polystyrene (product number 44,114-7, Aldrich Inc., average molecular weight ca. 350.000) was dissolved in 50 ml toluene.

Step 2

This solution was spin-coated for 40 seconds at 4000 rpm onto the substrate, forming a thin polymer film. A post-bake to remove the solvent was usually not applied.

Step 3

One drop of ctDNA was applied to the surface of the polymer film. This drop was spin-coated at 3000-4000 rpm for about 40 s. After this, one drop of water was applied and spin-coated to wash the surface and remove any buffer salts.

Step 4

Version a), THPAuNP in Pure Water

One drop of THPAuNPs in water (for synthesis details see Example 2 below) was applied to the sample surface and remained there for at least several seconds up to 1 h, preferably for 5 to 10 minutes.

Version b) THPAuNP in an Alcohol/Water Mixture 1 ml of the THPAuNP sol was diluted with 10 ml ethanol and cooled for 2 h at 4° C. to precipitate the particles. The mixture was centrifuged at 5000 rpm for 10 minutes and the supernatant was removed. The precipitated nanoparticles were redissolved in 0.05-1.0 ml of water, and an appropriate volume of methanol or ethanol was added to give a total volume of 1.0 ml. One drop of this solution was applied to the sample surface and remained there for at least several seconds, preferably for up to 5 to 10 minutes.

Finally, the sample surface was washed using one drop of water and subsequently it was dried using the stream of compressed air. Both versions lead to the desired result of attachment of metallic nanoparticles to the DNA. Version b) however, seem to give more reproducible results, but as a slight disadvantage, more experimental effort is needed in this case.

Step 5

One drop of commercially available electroless plating solution (GoldEnhance-LM™, catalog number 2112, www.nanoprobes.com, Nanoprobes Inc., USA) was applied to the substrate surface for at least several seconds minutes, preferably for about 5 minutes. In this step, the initially attached NPs were grown to a larger size in order to form a continuous metallic chain. After this, the sample surface was washed using one drop of water and then it was dried using the stream of compressed air.

EXAMPLE 2

Nanoparticle Synthesis

The THPAuNPs were synthesized following the publication by Duff et al., J. Chem. Soc., Chem. Commun. (1993) 96; Duff et al., Langmuir 9 (993) 2301; W. Vogel, Langmuir 11 (1995) 401. Their standard preparation, which involves adding a solution of $HAuCl_4$ to a solution of hydrolyzed tetrakis (hydroxymethyl)phosphonium chloride (THPC), gives an aqueous colloidal sol of THPAuNPs with a mean particle diameter of ca 1.5 nm.

In detail, the following reagents were added successively to a round-bottomed glass flask with constant magnetic stirring at room temperature: 18.5 ml water, 1.5 of aqueous 0.2 M NaOH, 0.5 ml of aqueous 0.13 M THPC, and 4.5 ml of aqueous 0.011 M $HAuCl_4$. The THPC and $HAuCl_4$ solutions were added to the reaction vessel within 2-10 minutes after they were prepared. THPAuNP sols were stored refrigerated in polypropylene containers.

EXAMPLE 3

Surface Investigations

Figure 1:
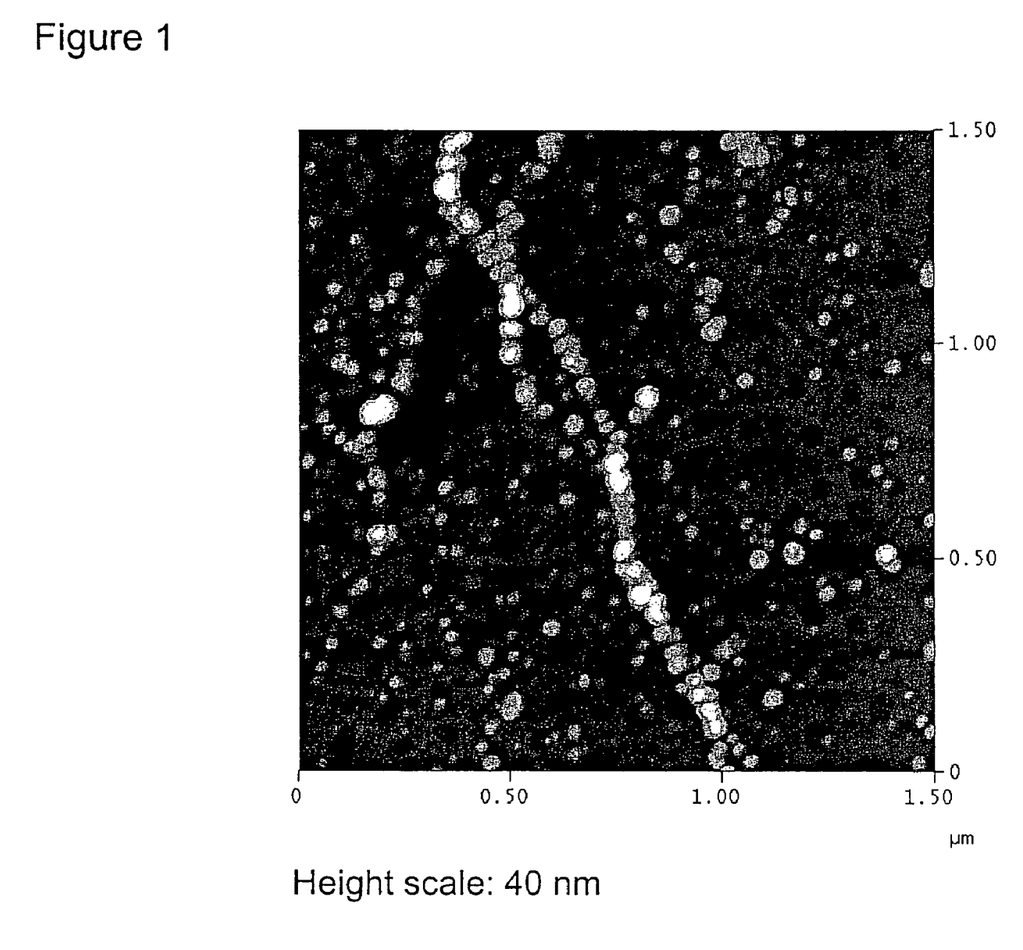
FIG. 1 shows an AFM picture of metallized DNA ladder on polystyrene according to one embodiment of the method according to the present invention.
Figure 2:
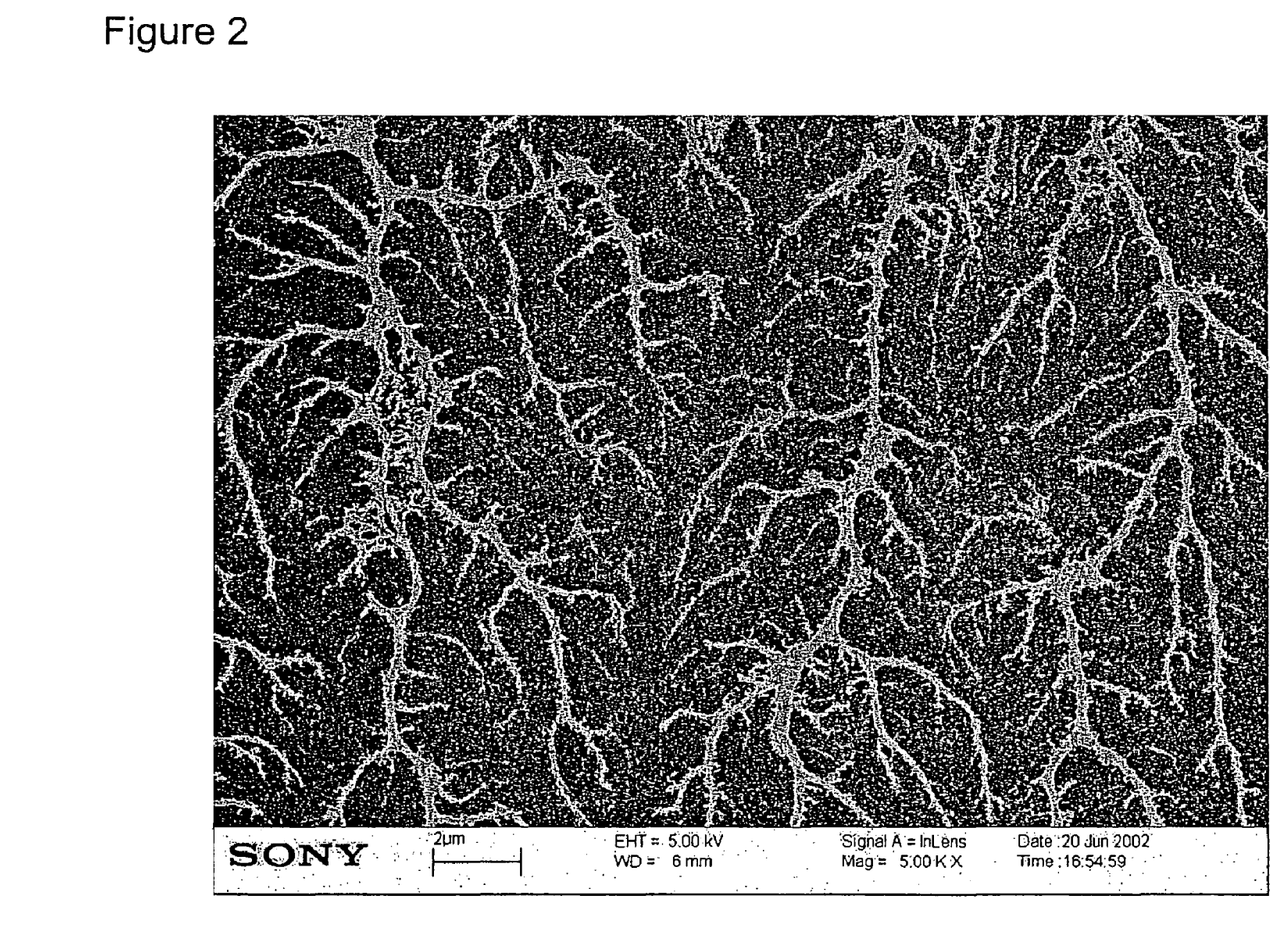
FIG. 2 shows an SEM picture of a DNA-on-polystyrene sample treated according to one embodiment of the method according to the present invention.

FIG. 1 shows an atomic force microscopy (AFM) image of a sample which was treated according to Step 1, 2, 3, 4 (without Step 5), using the DNA ladder as macromolecule. The picture clearly shows that NPs are attached to the DNA molecules. Samples, which were treated by including Step 5 were usually investigated using a scanning electron microscope[22] (SEM). FIG. 2 shows the SEM picture of the resulting sample surface of a polystyrene surface, which was processed by applying Step 1, 2, 3, 4a, 5. The NP solution was applied for 10 minutes and the electroless plating step was performed for 5 minutes. The picture shows a high density of stretched and metallised DNA molecules. The DNA molecules seem to mainly attach to the surface at their ends.

Figure 3:
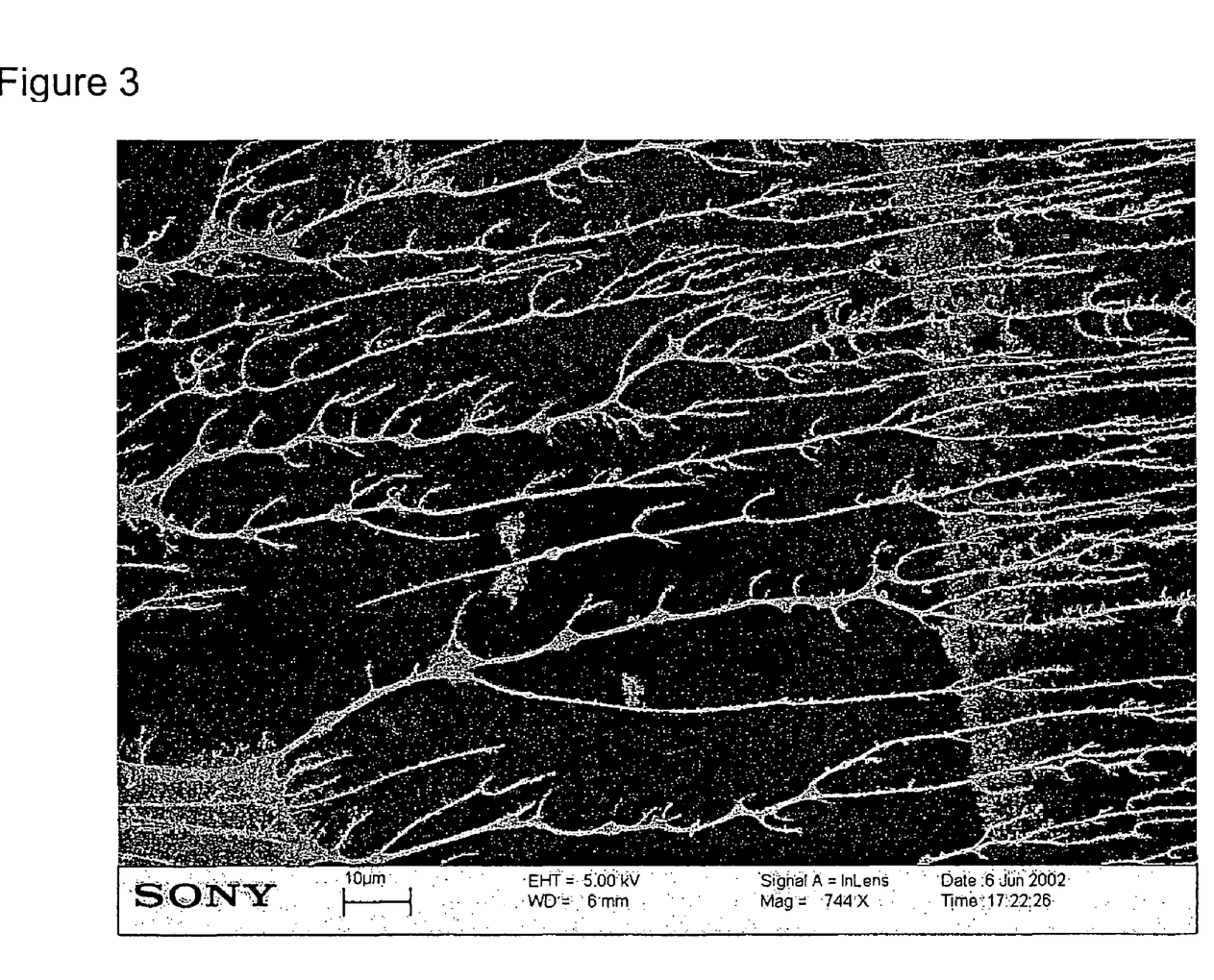
FIG. 3 shows an SEM picture of a DNA-on-polystyrene sample treated according to one embodiment of the method according to the present invention.

FIG. 3 shows an SEM picture of the resulting polystyrene surface, which was processed by applying Step 1, 2, 3, 4a, 5. In this case, a 95% methanol/water mixture was used for the solvent of the THPAuNPs. The NP solution was applied for 10 minutes and the electroless plating step was performed for 6 minutes. Tens of μm long and completely metallized DNA-templated wires can be identified on this picture.

Figure 4:
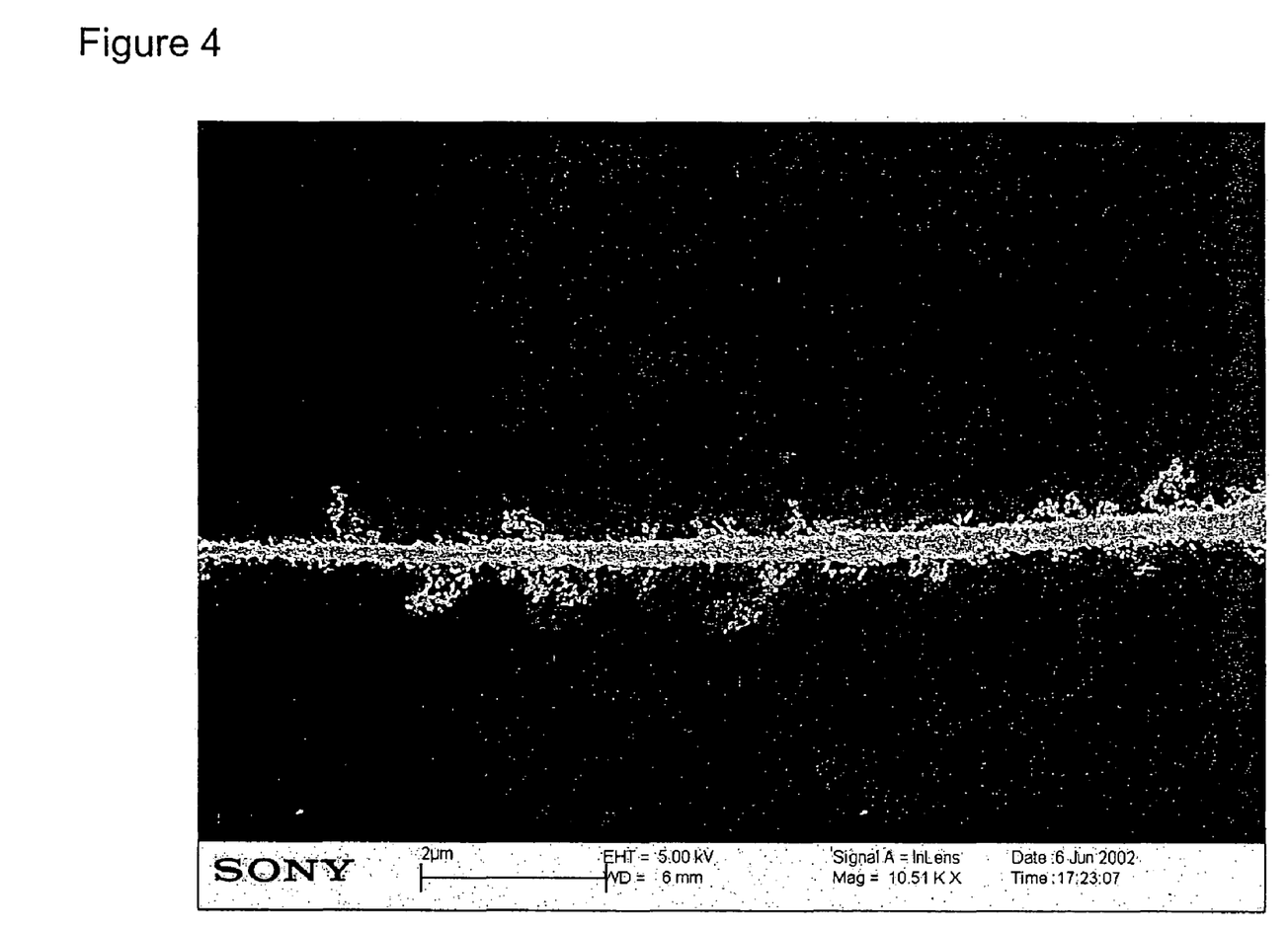
FIG. 4 shows an SEM inlens-picture of a DNA wire segment treated according to one embodiment of the method according to the present invention.
Figure 5:
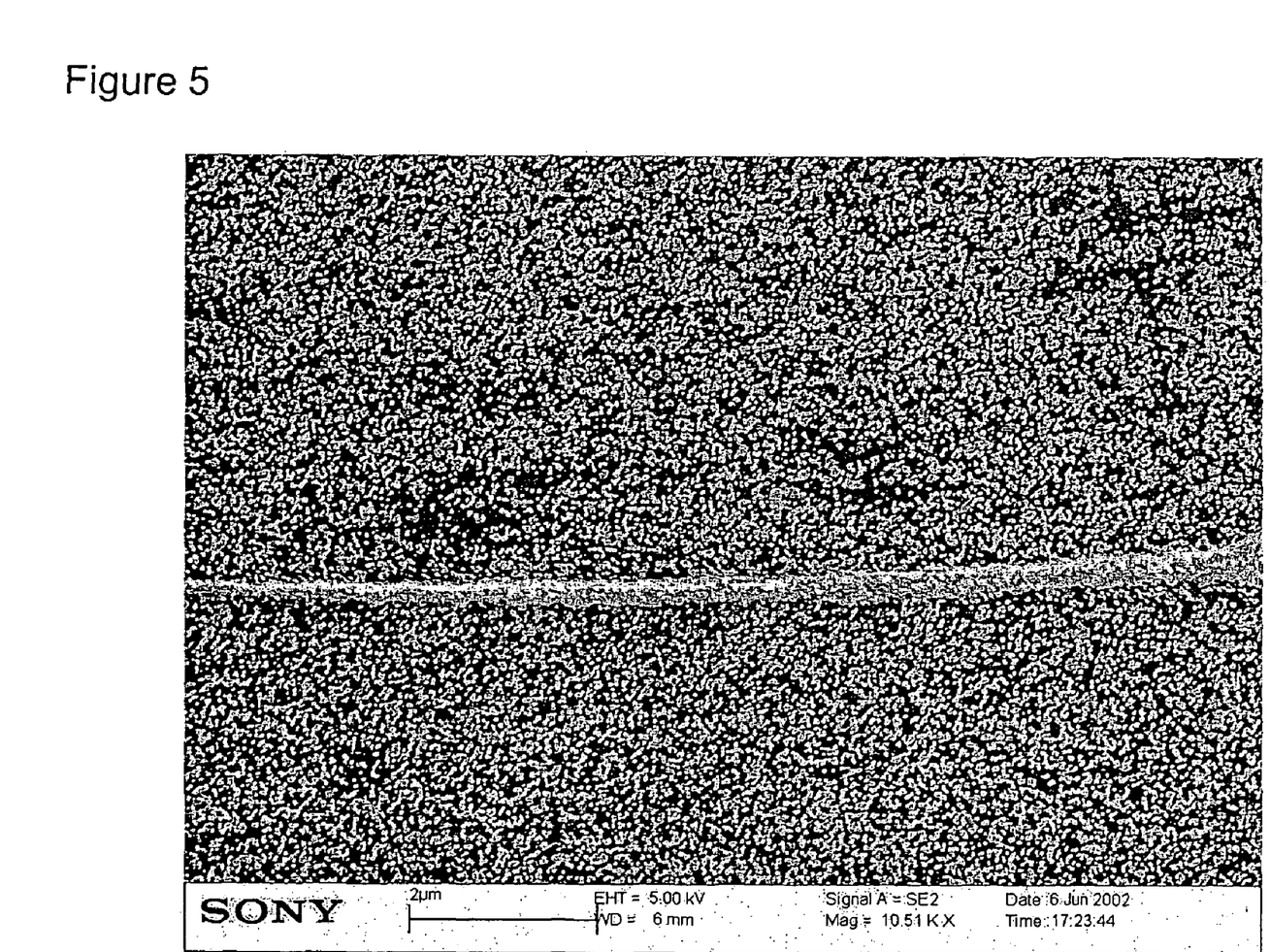
FIG. 5 shows an SEM SE2-picture of a DNA wire segment treated according to one embodiment of the method according to the present invention.

FIG. 4 and FIG. 5 were taken from the same sample shown in FIG. 3. FIG. 4 shows the SEM picture of one segment of the metallised DNA, which was taken by using the Inlens-detector. This detector collects mainly the reflected electrons, which carry information on the conductivity of the sample surface. Thus, the picture data indicate that the wire is a good electrical conductor (large detector signal). In addition, a few parts of the attached branches of NP's do also conduct, while the background appears dark (small detector signal). FIG. 5 shows a SEM picture of the same region, which was taken by using the SE2-detector. This detector collects the backscattered electrons, which carry data on the topology of the surface. This picture shows a large density of excess NPs, which however, according to FIG. 4, do not significantly contribute to the electrical conductivity.

These results turned out to be much more reproducible than the results based on the same metallization approach, but performed on hydrophilic (oxygen-plasma treated) $SiO_2$ substrate. In fact, Step 4, Version a) led to reliable and reproducible results only on hydrophobic polymer surfaces. This means that by using the inventive method, hydrophilic species can be reliably attached to hydrophilic macromolecules immobilised on a hydrophobic surface. It needs to be pointed out, however, that, in principle, the opposite case of attachment of hydrophobic species to hydrophobic macromolecules immobilised on hydrophilic surfaces should also be effective. No specific example, however, can be given for this case at this point in time.

EXAMPLE 4

General Tendencies (Adjustment of Process Parameters)

Excess Particles

Figure 6:
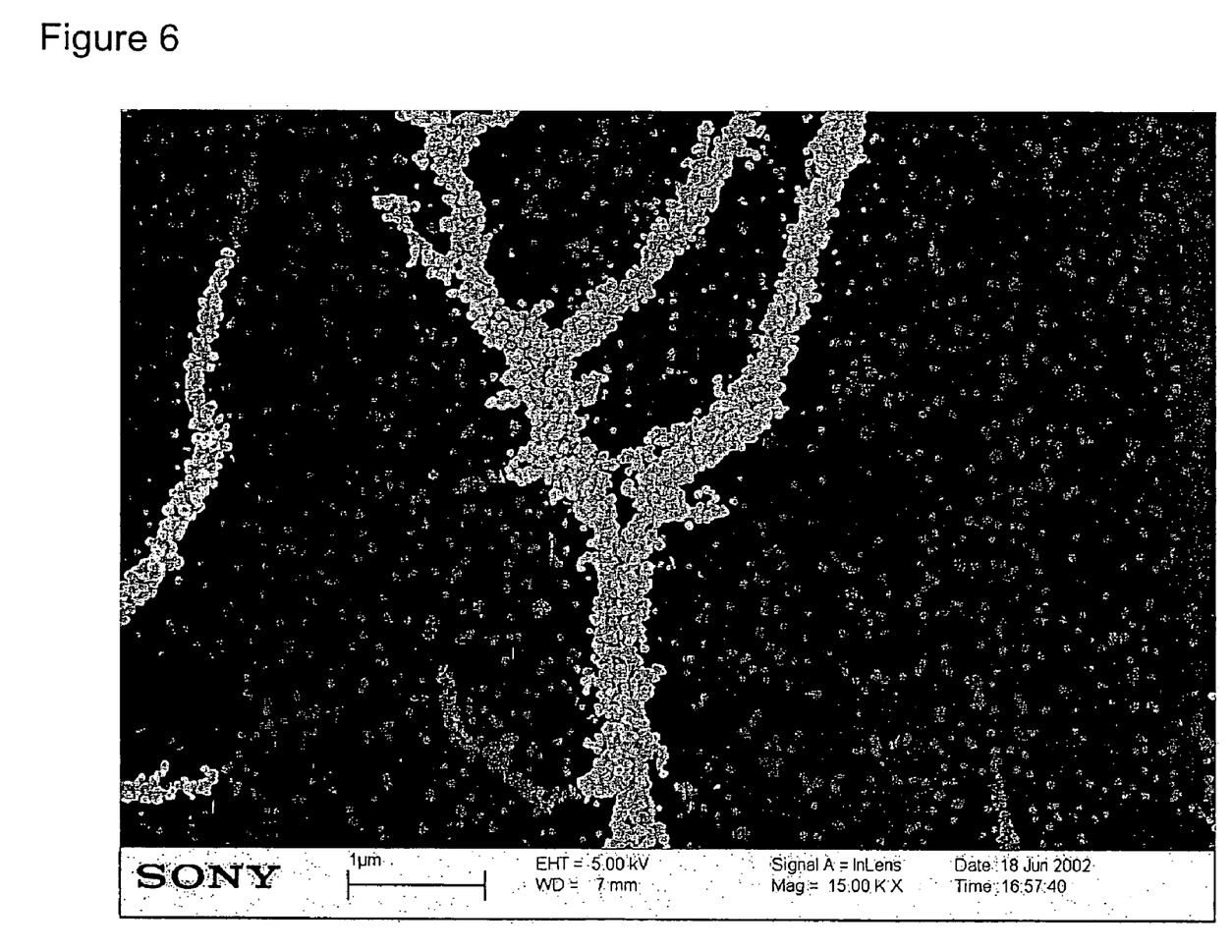
FIG. 6 shows an SEM picture of a DNA-on-polystyrene sample treated according to one embodiment of the method according to the present invention using a 100 times diluted nanoparticle (NP) solution.

Reducing the concentration of the NP/water solution decreased the density of excess particles on the substrate surface. As shown on FIG. 6, at a 100 times dilution, the density of excess particles was clearly reduced and at the same time good templating properties were still observed. This sample was treated according to Step 1, 2, 3, 4a, 5. The solvent was a 75% methanol/water mixture, the treatment time in Step 4b was 20 minutes and the electroless plating time in Step 5 was 5 minutes.

Wire Mean Diameter

The mean diameter of the DNA wires was about 200 to 500 nm, which is significantly higher than the average mean diameter that were usually observed by using other metallization approaches or this approach on a hydrophilic substrate. The reason for this is that the DNA molecules tend to form intertwined and therefore relatively thick rope structures on hydrophobic polystyrene. A reduction of the DNA concentration could reduce the rope mean diameter. In addition, the final mean diameter resulting from metallization could be further reduced by decreasing the duration of the electro-less plating step (Step 5).

Process Time

A complete metallization of DNA molecules is achievable using a short NP treatment of the DNA of less than 5 minutes (plus the time for the electroless plating step). The exact time for getting an almost complete metallization was not precisely determined yet, but is estimated to be about 2 minutes.

The features of the present invention disclosed in the specification, the claims and/or in the accompanying drawings, may, both separately and in any combination thereof, be material for realizing the invention in various forms thereof.

The invention claimed is:

1. A method of attaching hydrophilic species to hydrophilic macromolecules immobilized on a hydrophobic surface, said method comprising the steps:
   (i) providing a hydrophobic surface,
   (ii) immobilizing hydrophilic macromolecules on the hydrophobic surface,
   (iii) exposing the hydrophilic macromolecules immobilized on the hydrophobic surface to hydrophilic species, whereby the hydrophilic species are attached to the hydrophilic macromolecules.

2. A method according to claim 1, characterized in that the hydrophilic species comprises nanoparticles.

3. A method according to claim 1, characterized in that the hydrophilic species is in solution.

4. A method according to claim 1, comprising the additional step:
   (iv) growing the attached hydrophilic species to a larger size.

5. A method according to claim 4, characterized in that growing the attached hydrophilic species to a larger size is achieved by exposing the attached hydrophilic species to an electroless plating solution.

6. A method according to claim 1, characterized in that immobilizing the hydrophilic macromolecules on the hydrophobic surface occurs by applying the hydrophilic macromolecules to the hydrophobic surface.

7. A method according to claim 6, characterized in that applying the hydrophilic macromolecules to the hydrophobic surface occurs by a process selected from spin-coating, dip-coating, drop-casting, stamping, molecular combing, spraying-techniques, inkjet-printing and doctor-blading.

8. A method according to claim 1, characterized in that exposing the hydrophilic macromolecules to hydrophilic species, whereby the hydrophilic species are attached to the hydrophilic macromolecules, occurs over a period of time between 1 second and 120 minutes.

9. A method according to claim 8, characterized in that exposing the hydrophilic macromolecules to hydrophilic species occurs over a period of time between 10 seconds and 10 minutes.

10. A method according to claim 3, characterized in that the solution is a solution of the hydrophilic species in water or of the hydrophilic species in a water-miscible organic solvent/water mixture.

11. A method according to claim 1, characterized in that water has a contact angle on the hydrophobic surface in the range of from 30° to 110°.

12. A method according to claim 11, characterized in that water has a contact angle on the hydrophobic surface in the range of from 60° to 110°.

13. A method according to claim 1, characterized in that the hydrophilic species is selected from the group comprising water soluble metal nanoparticles, semiconductor nanoparticles and dielectric (insulator) nanoparticles, hydrophilic clusters and metallic complexes.

14. A method according to claim 2, characterized in that the nanoparticle has a core and comprises a metal or metal oxide in the core, where the metal is selected from the group comprising Fe, Co, Ni, Cu, Ru, Rh, Pd, Os, Ir, Ag, Pt, Au or combinations, especially alloys of these metals.

15. A method according to claim 1, characterized in that the hydrophilic macromolecules are selected from the group comprising nucleic acids, proteins, dendrimers, latex spheres, polyelectrolytes, and water-soluble polymers.

16. A method according to claim 15, characterized in that the nucleic acid is selected from the group comprising DNA, RNA, PNA, CNA, oligonucleotides, oligonucleotides of RNA, A-DNA, B-DNA, Z-DNA, polynucleotides of DNA, polynucleotides of RNA, T-junctions of nucleic acids, triplexes of nucleic acid, quadruplexes of nucleic acids, domains of non-nucleic acid polymer-nucleic acid block-copolymers and combinations thereof.

17. A method according to claim 16, characterized in that the nucleic acid is double-stranded or single-stranded.

18. A method according to claim 1, characterized in that the hydrophilic species is selected from the group comprising tris(hydroxymethyl)phosphine-gold nanoparticles (THPAuNPs).

19. A method according to claim 5, characterized in that the electroless plating solution comprises a gold salt and a reducing agent.

* * * * *